(12) United States Patent
Anderson et al.

(10) Patent No.: US 10,390,768 B2
(45) Date of Patent: Aug. 27, 2019

(54) DEVICES, SYSTEMS, AND METHODS FOR VISUALLY DEPICTING A VESSEL AND EVALUATING TREATMENT OPTIONS

(71) Applicant: Volcano Corporation, San Diego, CA (US)

(72) Inventors: David Anderson, Temecula, CA (US); Justin Davies, London (GB)

(73) Assignees: Volcano Corporation, San Diego, CA (US); Imperial College of Science, Technology and Medicine, South Kensington, London (GB)

( * ) Notice: Subject to any disclaimer, the term of this patent is extended or adjusted under 35 U.S.C. 154(b) by 1000 days.

(21) Appl. No.: 14/550,369

(22) Filed: Nov. 21, 2014

(65) Prior Publication Data

US 2015/0080749 A1 Mar. 19, 2015

Related U.S. Application Data

(63) Continuation of application No. 14/239,734, filed as application No. PCT/US2012/051566 on Aug. 20, 2012, now abandoned.

(Continued)

(51) Int. Cl.
| | |
|---|---|
| *A61B 5/02* | (2006.01) |
| *A61B 5/00* | (2006.01) |
| *A61B 5/0215* | (2006.01) |
| *A61B 5/01* | (2006.01) |
| *A61B 5/0205* | (2006.01) |

(Continued)

(52) U.S. Cl.
CPC .............. *A61B 5/743* (2013.01); *A61B 5/015* (2013.01); *A61B 5/02007* (2013.01); *A61B 5/02014* (2013.01); *A61B 5/0215* (2013.01); *A61B 5/02055* (2013.01); *A61B 5/02158* (2013.01); *A61B 5/4839* (2013.01); *A61B 5/7278* (2013.01); *A61B 17/22* (2013.01); *A61F 2/82* (2013.01); *A61B 5/6876* (2013.01);
(Continued)

(58) Field of Classification Search
CPC .. A61B 5/00; A61B 17/22; A61B 5/01; A61B 5/02; A61B 5/0205; A61B 5/0215; A61B 5/02007; A61B 5/02014; A61B 5/02158; A61B 5/7278; A61B 5/4839; A61B 5/02055; A61B 5/015; A61B 5/07; A61F 2/82
See application file for complete search history.

(56) References Cited

U.S. PATENT DOCUMENTS

| | | |
|---|---|---|
| 5,775,338 A | 7/1998 | Hastings |
| 6,062,089 A | 5/2000 | Ichihashi |

(Continued)

FOREIGN PATENT DOCUMENTS

| | | |
|---|---|---|
| EP | 2298162 | 3/2011 |
| WO | WO 00-53081 | 9/2000 |

(Continued)

OTHER PUBLICATIONS

SmartFlow™ Integrated Lumen Physiology, Version 5.0, Operator's Manual, Apr. 2001.

(Continued)

*Primary Examiner* — Eric J Messersmith

(57) ABSTRACT

Devices, systems, and methods for visually depicting a vessel and evaluating treatment options are disclosed.

41 Claims, 10 Drawing Sheets

Related U.S. Application Data

(60) Provisional application No. 61/525,736, filed on Aug. 20, 2011.

(51) Int. Cl.
    *A61B 17/22*      (2006.01)
    *A61F 2/82*      (2013.01)
    *G16H 50/50*      (2018.01)

(52) U.S. Cl.
    CPC ............... *A61B 2017/22001* (2013.01); *A61B 2562/0247* (2013.01); *G16H 50/50* (2018.01)

(56) References Cited

U.S. PATENT DOCUMENTS

| | | |
|---|---|---|
| 6,106,476 A | 8/2000 | Corl et al. |
| 6,129,674 A | 10/2000 | Ovadia-Blechman et al. |
| 6,190,355 B1 | 2/2001 | Hastings |
| 6,193,669 B1 | 2/2001 | Degany et al. |
| 6,296,615 B1 | 10/2001 | Brockway et al. |
| 6,343,514 B1 | 2/2002 | Smith |
| 6,354,999 B1 | 3/2002 | Degany et al. |
| 6,409,677 B1 | 6/2002 | Tulkki |
| 6,471,656 B1 | 10/2002 | Shalman et al. |
| 6,558,334 B2 | 5/2003 | Shalman et al. |
| 6,565,514 B2 | 5/2003 | Svanerudh et al. |
| 6,585,660 B2 | 7/2003 | Dorando et al. |
| 6,615,667 B2 | 9/2003 | Smith |
| 6,659,959 B2 | 12/2003 | Brockway et al. |
| 6,663,570 B2 | 12/2003 | Mott et al. |
| 6,697,667 B1 | 2/2004 | Lee et al. |
| 6,716,178 B1 | 4/2004 | Kilpatrick et al. |
| 6,754,608 B2 | 6/2004 | Svanerudh et al. |
| 6,868,736 B2 | 3/2005 | Sawatari et al. |
| 7,134,994 B2 | 11/2006 | Alpert et al. |
| 7,274,956 B2 | 9/2007 | Mott et al. |
| RE39,863 E | 10/2007 | Smith |
| 7,329,223 B1 | 2/2008 | Ainsworth et al. |
| 7,481,774 B2 | 1/2009 | Brockway et al. |
| 7,532,920 B1 | 5/2009 | Ainsworth et al. |
| 7,632,304 B2 | 12/2009 | Park |
| 7,693,563 B2 | 4/2010 | Suresh |
| 7,775,988 B2 | 8/2010 | Pijls |
| 7,783,338 B2 | 8/2010 | Ainsworth et al. |
| 7,814,635 B2 | 10/2010 | Gordon et al. |
| 7,828,841 B2 | 11/2010 | Mathis et al. |
| 7,828,842 B2 | 11/2010 | Nieminen et al. |
| 7,828,843 B2 | 11/2010 | Alferness et al. |
| 7,853,626 B2 | 12/2010 | Jung et al. |
| 7,887,582 B2 | 2/2011 | Mathis et al. |
| 8,006,594 B2 | 8/2011 | Hayner et al. |
| 8,029,447 B2 | 10/2011 | Kanz et al. |
| 8,062,358 B2 | 11/2011 | Mathis et al. |
| 8,075,608 B2 | 12/2011 | Gordon et al. |
| 8,157,742 B2 | 4/2012 | Taylor |
| 2002/0052553 A1 | 5/2002 | Shalman et al. |
| 2002/0059827 A1 | 5/2002 | Smith |
| 2002/0065472 A1 | 5/2002 | Alpert et al. |
| 2002/0072880 A1 | 6/2002 | Svanerudh |
| 2002/0173724 A1 | 11/2002 | Reuter et al. |
| 2003/0032886 A1 | 2/2003 | Degertekin et al. |
| 2003/0033095 A1 | 2/2003 | Svanerudh |
| 2003/0159518 A1 | 8/2003 | Ahmed et al. |
| 2003/0163052 A1 | 8/2003 | Ahmed et al. |
| 2003/0191400 A1 | 10/2003 | Alpert et al. |
| 2003/0195428 A1 | 10/2003 | Pijls |
| 2003/0216621 A1 | 11/2003 | Naghavi et al. |
| 2004/0082866 A1 | 4/2004 | Naghavi et al. |
| 2004/0158321 A1 | 8/2004 | Smith et al. |
| 2005/0121734 A1 | 6/2005 | Naghavi et al. |
| 2006/0052700 A1 | 3/2006 | Jung et al. |
| 2006/0074318 A1 | 4/2006 | Jung et al. |
| 2006/0106321 A1 | 5/2006 | Lewinsky et al. |
| 2006/0241505 A1 | 10/2006 | Ahmed et al. |
| 2007/0060822 A1 | 3/2007 | Patangay et al. |
| 2007/0078352 A1 | 4/2007 | Lieu et al. |
| 2007/0225606 A1 | 9/2007 | Naghavi et al. |
| 2007/0225614 A1 | 9/2007 | Kanz et al. |
| 2007/0255145 A1 | 11/2007 | Naghavi et al. |
| 2008/0027330 A1 | 1/2008 | Camus et al. |
| 2008/0081957 A1 | 4/2008 | Lieu et al. |
| 2008/0082522 A1 | 4/2008 | Smith |
| 2008/0082582 A1 | 4/2008 | Knight et al. |
| 2008/0101532 A1 | 5/2008 | Tkaczyk et al. |
| 2008/0139951 A1 | 6/2008 | Naghavi et al. |
| 2008/0213165 A1 | 9/2008 | Belardinelli et al. |
| 2008/0228086 A1 | 9/2008 | Johnson et al. |
| 2008/0255471 A1 | 10/2008 | Tiensuu et al. |
| 2008/0269572 A1 | 10/2008 | Kassab |
| 2008/0281205 A1 | 11/2008 | Voros et al. |
| 2008/0292049 A1 | 11/2008 | Manstrom et al. |
| 2009/0081120 A1 | 3/2009 | Belleville et al. |
| 2009/0082678 A1 | 3/2009 | Shalman et al. |
| 2009/0088650 A1 | 4/2009 | Corl |
| 2009/0234231 A1 | 9/2009 | Brockway et al. |
| 2010/0081941 A1 | 4/2010 | Alpert et al. |
| 2010/0086483 A1 | 4/2010 | Mott et al. |
| 2010/0109104 A1 | 5/2010 | Reuter et al. |
| 2010/0152607 A1 | 6/2010 | Degertekin et al. |
| 2010/0156898 A1 | 6/2010 | Svanerudh |
| 2010/0234698 A1 | 9/2010 | Manstrom |
| 2010/0241008 A1 | 9/2010 | Ahmed et al. |
| 2010/0280396 A1 | 11/2010 | Zhang |
| 2010/0286537 A1 | 11/2010 | Pijls |
| 2011/0066047 A1 | 3/2011 | Belleville et al. |
| 2011/0071404 A1* | 3/2011 | Schmitt ................ A61B 5/0066 600/479 |
| 2011/0071407 A1 | 3/2011 | Hubinette et al. |
| 2011/0085977 A1 | 4/2011 | Rosenmeier |
| 2011/0137140 A1 | 6/2011 | Tearney et al. |
| 2011/0137210 A1 | 6/2011 | Johnson |
| 2011/0178383 A1 | 7/2011 | Kassab |
| 2011/0178413 A1 | 7/2011 | Schmitt et al. |
| 2011/0178417 A1 | 7/2011 | Kassab |
| 2011/0196255 A1 | 8/2011 | Kassab |
| 2011/0245693 A1 | 10/2011 | Hastings et al. |
| 2011/0251497 A1 | 10/2011 | Corl et al. |
| 2011/0263986 A1 | 10/2011 | Park et al. |
| 2011/0306867 A1 | 12/2011 | Gopinathan et al. |
| 2011/0319752 A1 | 12/2011 | Steinberg et al. |
| 2011/0319773 A1 | 12/2011 | Kanz et al. |
| 2012/0004529 A1 | 1/2012 | Tolkowsky et al. |
| 2012/0004537 A1 | 1/2012 | Tolkowsky et al. |
| 2012/0029339 A1 | 2/2012 | Cohen et al. |
| 2012/0041318 A1 | 2/2012 | Taylor |
| 2012/0041319 A1 | 2/2012 | Taylor et al. |
| 2012/0041320 A1 | 2/2012 | Taylor |
| 2012/0041321 A1 | 2/2012 | Taylor |
| 2012/0041322 A1 | 2/2012 | Taylor et al. |
| 2012/0041323 A1 | 2/2012 | Taylor et al. |
| 2012/0041324 A1 | 2/2012 | Taylor |
| 2012/0041735 A1 | 2/2012 | Taylor |
| 2012/0041739 A1* | 2/2012 | Taylor ................ A61B 5/02007 703/11 |
| 2012/0052918 A1 | 3/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0065514 A1 | 3/2012 | Naghavi et al. |
| 2012/0065623 A1 | 3/2012 | Nelson, III et al. |
| 2012/0071782 A1 | 3/2012 | Patil et al. |
| 2012/0072190 A1 | 3/2012 | Sharma et al. |
| 2012/0101355 A1 | 4/2012 | Gopinathan et al. |
| 2012/0101369 A1 | 4/2012 | Patil et al. |
| 2012/0220883 A1 | 8/2012 | Manstrom et al. |

FOREIGN PATENT DOCUMENTS

| | | |
|---|---|---|
| WO | WO 2001/13779 | 3/2001 |
| WO | 2006041346 A1 | 4/2006 |
| WO | WO2006041346 | 4/2006 |
| WO | WO 2012/030882 A1 | 3/2010 |
| WO | 2011038044 A2 | 3/2011 |

(56) References Cited

FOREIGN PATENT DOCUMENTS

| WO | WO2011038044 | 3/2011 |
|---|---|---|
| WO | 2012093260 A1 | 7/2012 |
| WO | WO 2012/093266 | 12/2012 |

OTHER PUBLICATIONS

Florence Medical Innovations in Vascular Technology Business Plan, May 2002.
Florence Medical SmartFlow, CFR/FFR Manual, Mar. 2002.
SmartFlow CFR/FFR, Innovations in Vascular Technology, Model 2000, 2002, 6 pages.
Florence Medical, Annual Letter to Shareholders, May 17, 2001, 1 page.
Florence Medical LTD, Company Profile, May 2001, 4 pages.
SmartFlow™ Integrated Lumen Physiology for the Cathlab, SmartFlow CFR/FFR, Model 2000, Version 5.0 CFR/FFR, 2001, 2 pages.
Florence Medical Center 510(k) Summary SmartFlow™, May 14, 2001, 6 pages.
Florence Medical Center 510(k) Summary SmartFlow™, Oct. 2, 2001, 5 pages.
Florence Medical, Inc. News Release, Florence Medical Introduces SmartFlow Multiple Lesions™ Device at American College of Cardiology Meeting, Mar. 14, 2002, 2 pages.
The Free Library by Farlex, Florence Medical Introduces SmartFlow Multiple Lesion Device at American College of Cardiology Meeting, Mar. 14, 2002, 3 pages.
Florence Medical Innovations in Vascular Technology PowerPoint presentation, 2002.
Shalman, E., et al., Pergamon, Numberical modeling of the flow in stenosed coronary artery. The relationship between main hemodynamic parameters, Received Nov. 3, 2000, accepted Oct. 2, 2001.
Shalman, E., et al., Pergamon, Pressure-based simultaneous CFR and FFR measurements: understanding the physiology of a stenosed vessel, Received Jul. 18, 2000, accepted Oct. 6, 2000.
Grubert, Luis, M.D., et al., Simultaneous Assessment of Coronary Flow Reserve and Fractional Flow Reserve with a Novel Pressure-Based Method, Journal of Interventional Cardiology vol. 13, No. 5, 2000.
The International Bureau of WIPO, Notification Concerning Submission, Obtension or Transmittal of Priority Document for International Application No. PCT/GB2012/050024, dated Feb. 16, 2012, 1 page.
European Patent Office, The International Searching Authority, Notification of Transmittal of the International Search Report and the Written Opinion of the International Searching Authority, or the Declaration for International Application No. PCT/GB2012/050024, dated Apr. 19, 2012, 16 pages.
Davies, Justin E., et al., Evidence of a Dominant Backward-Propagating "Suction" Wave Responsible for Diastolic Coronary Filling in Humans, Attenuated in Left Ventricular Hypertrophy, Heart Failure, International Centre for Circulatory Health, St. Mary's Hospital and Imperial College, Department of Bioengineering, Physiological Flow Unit, and the Department of Clinical Engineering, Royal Brompton Hospital, London, United Kingdom, accepted Jan. 23, 2006, pp. 1768-1778.
International Searching Authority/Korean Intellectual Property Office, "Notification of Transmittal of the International Search Report and the Written Opinion of the International Searching Authority, or the Declaration", for PCT/US2012/051566, dated Mar. 29, 2013, 11 pages.
D.F. Young, N.R. Cholvin, and A.C. Roth, "Pressure Drop Across Artificially Induced Stenoses in the Femoral Arteries of Dogs", Circulation Research 1975; 36:735-743.
International Search Report and Written Opinion received in PCT Application No. PCT/US2013/057647, dated Dec. 12, 2013, 11 pages.
Russian Patent Office, "Office Action" for Application No. 2014110701, dated May 4, 2016, 17 pages with English translation.
Russian Patent Office, "Office Action" for Application No. 2014110702, dated May 4, 2016, 14 pages with English translation.
European Patent Office, "Extended European Search Report" for Application No. 16188188.3, dated Jan. 3, 2017, 10 pages.
Mynard JP et al: "Accurate Automatic Detection of End-Diastole From Left Ventricular Pressure Using Peak Curvature", IEEE Transactions on Biomedical Engineering, Nov. 1, 2008, 7 pages.
European Patent Office, "European Search Report" for Application No. 12826470.2, (PCT/US2012051570), dated Mar. 16, 2015, 8 pages.
European Patent Office, "European Search Report" for Application No. 12825326.7, (PCT/US201205156), dated Mar. 16, 2015, 7 pages.
Sen, Sayan et al "Development and Validation of a New Adenosine-Independent Index of Stenosis Severity from Coronary Wave-Intensity Analysis", Journal of the American College of Cardiology, vol. 59, No. 15, 2012.
Taylor, C.A. et al "Patient-Specific Modeling of Cardiovascular Mechanics", Annual Review of Biomedical Engineering, vol. 11, 2009.
Notice of Opposition in EP Application No. 12825326.7, dated Feb. 23, 2018.
Communication of a Notice of Opposition in EP Application No. 12825326.7, dated Mar. 1, 2018.
Taylor, C.A., "Patient-Specific Modeling of Cardiovascular Mechanics", Annual Review of Biomedical Engineering, vol. 11, Apr. 13, 2009, pp. 109-127.
Sen, Sayan, Development and Validation of a New Adenosine-Independent Index Stenosis Severity from Coronary Wave-Intensity Analysis, Journal of the American College of Cardiology, vol. 59, No. 15, 2012, pp. 1392-1402.

* cited by examiner

DEVICES, SYSTEMS, AND METHODS FOR VISUALLY DEPICTING A VESSEL AND EVALUATING TREATMENT OPTIONS

CROSS-REFERENCE TO RELATED APPLICATIONS

The present application is a continuation of U.S. Nonprovisional patent application Ser. No. 14/239,734 filed Feb. 19, 2014, which is a U.S. national stage application of Patent Cooperation Treaty Application No. PCT/US2012/051566, filed Aug. 20, 2012, which claims priority to and the benefit of U.S. Provisional Patent Application No. 61/525,736, filed Aug. 20, 2011, each of which is hereby incorporated by reference in its entirety.

TECHNICAL FIELD

The present disclosure relates generally to the assessment of vessels and, in particular, the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance predominantly by reducing the microcirculation resistance associated with the systolic portion of the heart cycle to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

Accordingly, there remains a need for improved devices, systems, and methods for assessing the severity of a blockage in a vessel and, in particular, a stenosis in a blood vessel. In that regard, there remains a need for improved devices, systems, and methods for assessing the severity of a stenosis in the coronary arteries that do not require the administration of hyperemic agents. Further, there remains a need for improved devices, systems, and methods for providing visual depictions of vessel that allow assessment of the vessel and, in particular, any stenosis or lesion of the vessel. Further still, there remains a need for improved devices, systems, and methods that simulate one or more available treatment options for the vessel.

SUMMARY

Embodiments of the present disclosure are configured to assess the severity of a blockage in a vessel and, in particular, a stenosis in a blood vessel. In some particular embodiments, the devices, systems, and methods of the present disclosure are configured to provide visual depictions of vessel that allow assessment of the vessel and, in particular, any stenosis or lesion of the vessel. Further, in some embodiments the devices, systems, and methods of the present disclosure are configured to simulate one or more treatment options for the vessel. The simulation of the treatment option(s) can be utilized to identify the most viable treatment option for a particular vessel.

In one embodiment, a method of evaluating a vessel of a patient is provided. The method includes introducing a first instrument into the vessel of the patient; introducing a second instrument into the vessel of the patient; moving the second instrument longitudinally through the vessel of the patient from a first position to a second position while maintaining the first instrument in a fixed longitudinal position with respect to the vessel; obtaining pressure measurements from the first and second instruments while the second instrument is moved longitudinally through the vessel; visually depicting the vessel on a display based on the obtained pressure measurements; and modifying the visual depiction of the vessel to simulate one or more treatment options. Systems for performing such methods are also provided.

In another embodiment, a method of evaluating a vessel of a patient is provided that includes introducing an instrument into the vessel of the patient; moving the instrument longitudinally through the vessel of the patient from a first position to a second position; obtaining pressure measurements from the instrument at a plurality of positions along the vessel as the instrument is moved longitudinally through the vessel; visually depicting the vessel on a display based on the pressure measurements obtained from the instrument; and modifying the visual depiction of the vessel to simulate one or more treatment options. Systems for performing such methods are also provided.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
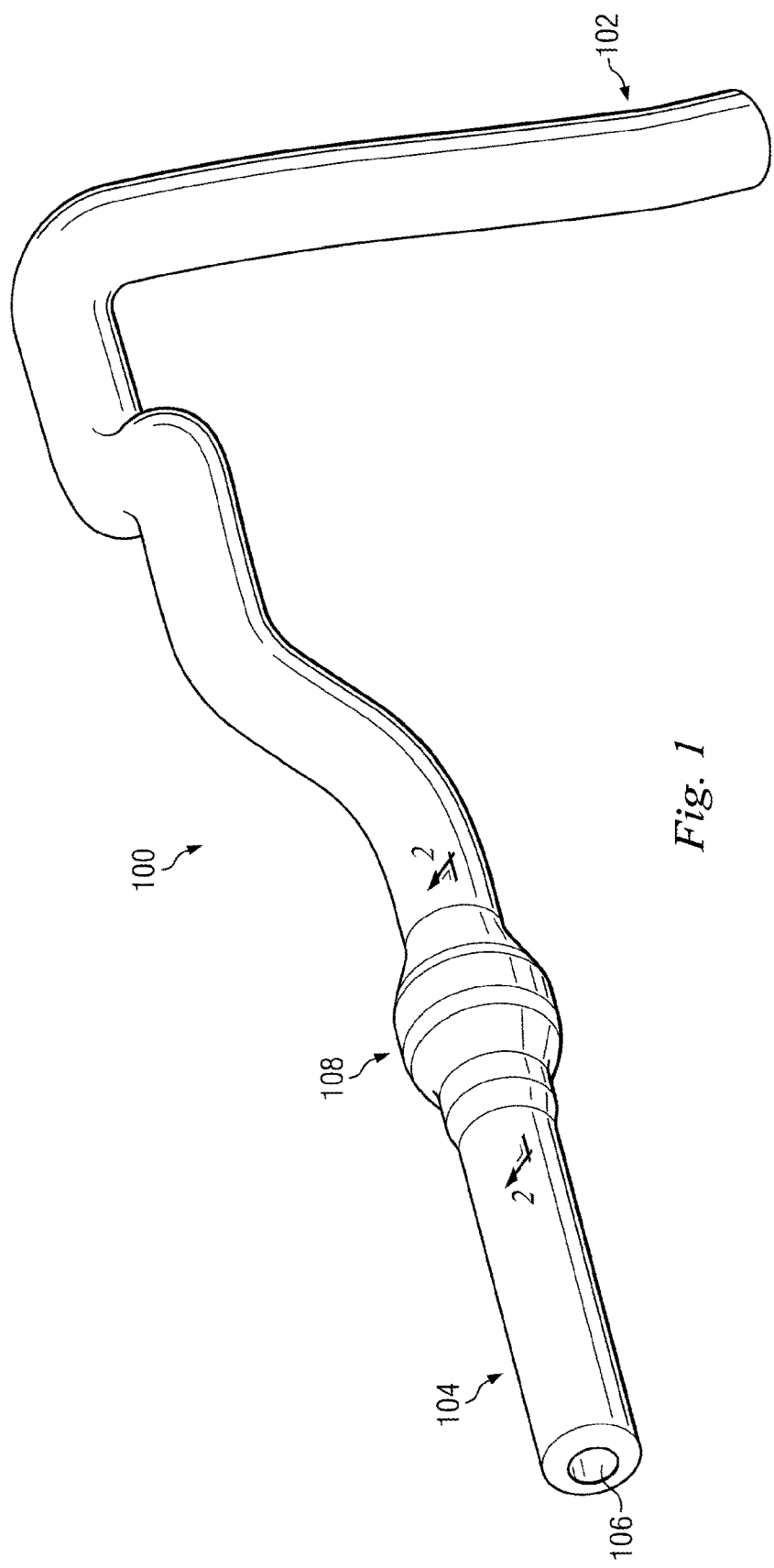
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
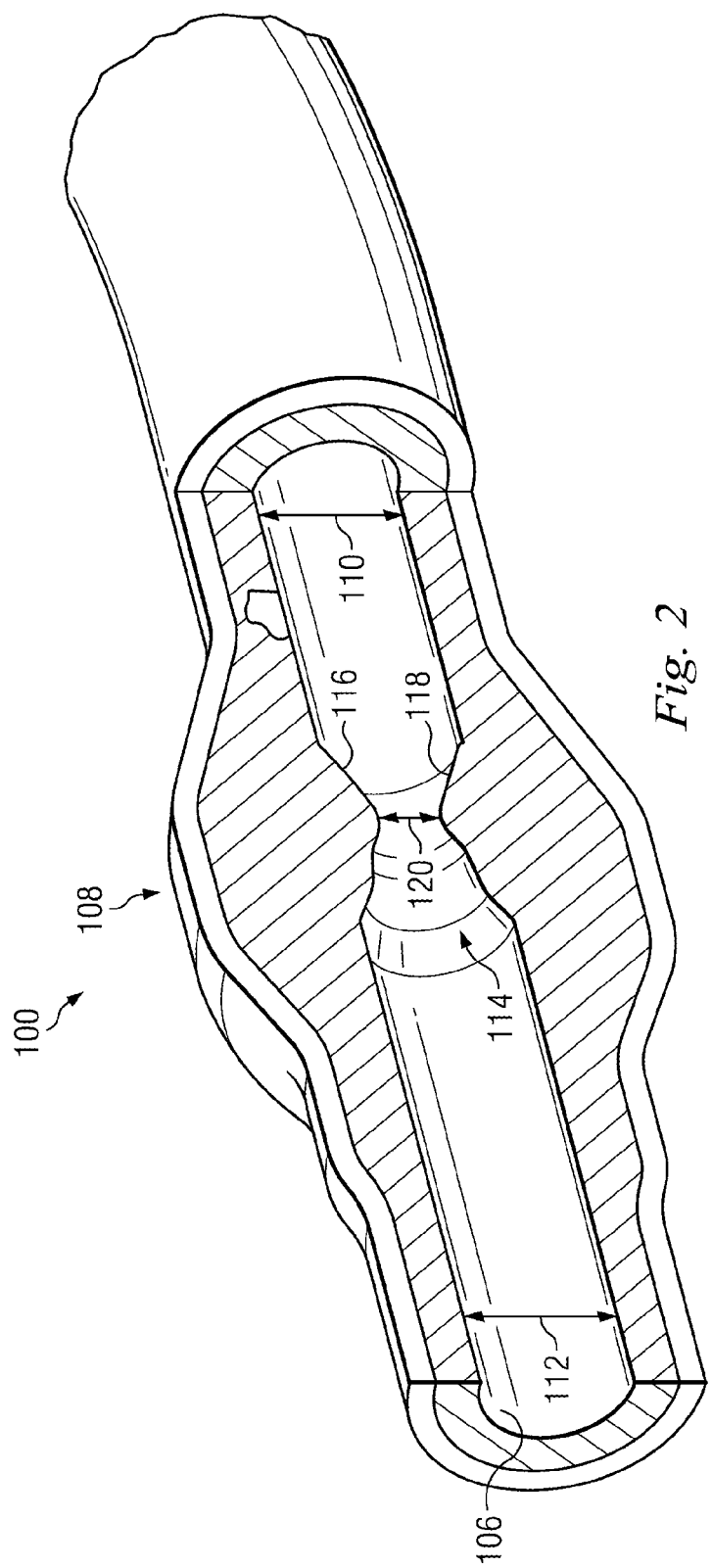
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
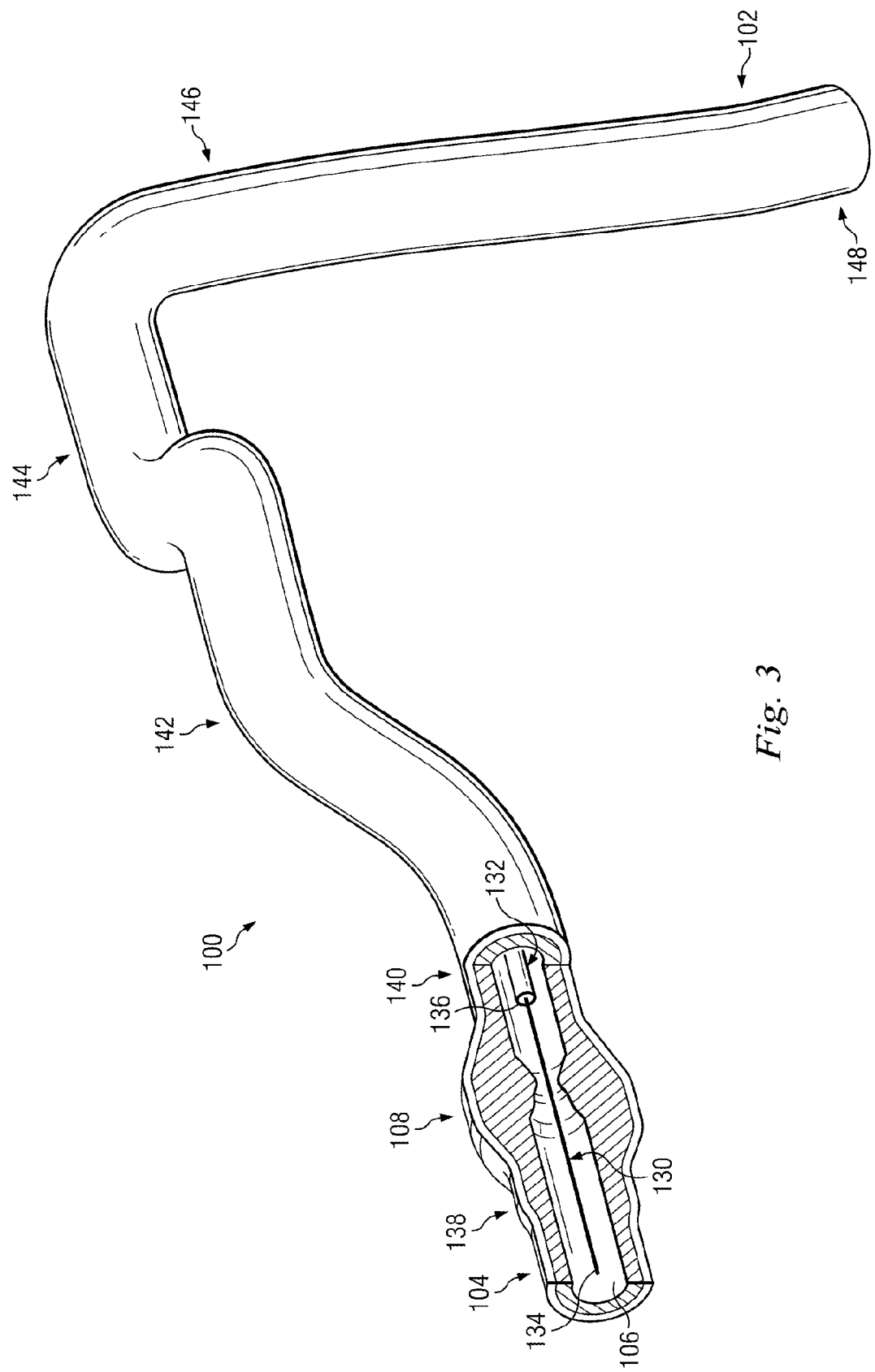
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

In some instances, use of a single instrument has a benefit in that it avoids issues associated with variations in pressure measurements of one instrument relative to another over time, which is commonly referred to as drift. In that regard, a major source of drift in traditional Fractional Flow Reserve (FFR) measurements is divergence in the pressure reading of a guidewire relative to the pressure reading of a guide catheter. In that regard, because FFR is calculated as the ratio of the pressure measurement obtained by the guidewire to the pressure measurement obtained by the catheter, this divergence has an impact on the resulting FFR value. In contrast, where a single instrument is utilized to obtain pressure measurements as it is moved through the vessel, drift is negligible or non-existent. For example, in some instances, the single instrument is utilized to obtain relative changes in pressures as it is moved through the vessel such that the time period between pressure measurements is short enough to prevent any impact from any changes in pressure sensitivity of the instrument (e.g., less than 500 ms, less than 100 ms, less than 50 ms, less than 10 ms, less than 5 ms, less than 1 ms, or otherwise).

Figure 4:
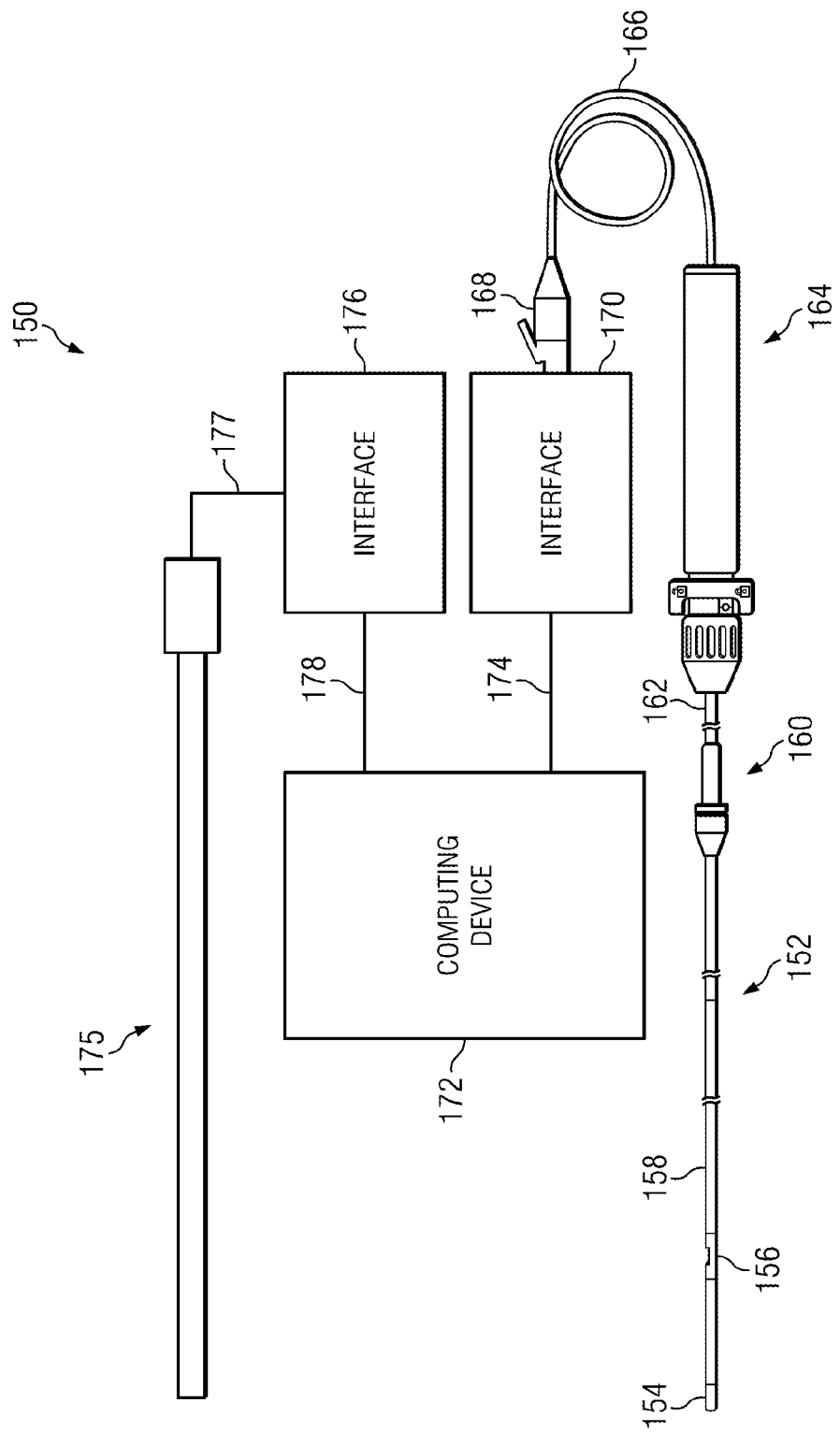
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Figure 5:
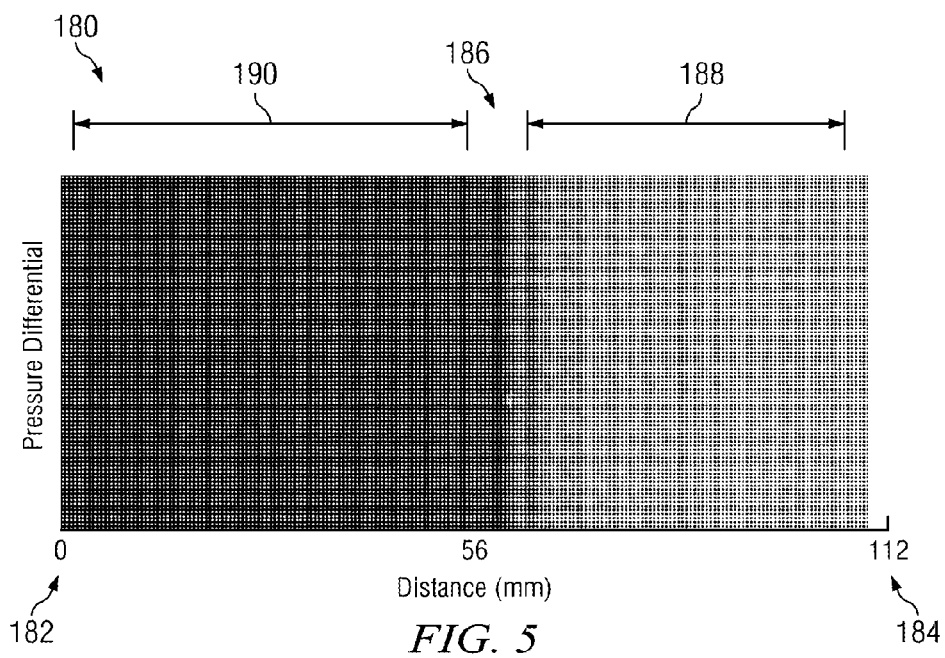
FIG. 5 is a visual depiction of a vessel profile based on pressure measurements according to an embodiment of the present disclosure.

Referring now to FIGS. 5-8, shown therein are various visual depictions of a vessel profile based on pressure measurements according to embodiments of the present disclosure. Referring more specifically to FIG. 5, shown therein is a visual representation 180 of a vessel. In that regard, visual representation 180 illustrates approximately a 112 mm segment of the vessel between points 182 and 184. In that regard, point 182 is representative of a starting position of an instrument within the vessel while point 184 is representative of an ending position of the instrument within the vessel after movement of the instrument longitudinally along the lumen of the vessel. Accordingly, in the instance of a pullback of the instrument, point 182 is distal of point 184 within the vessel. On the other hand, in the instance where the instrument pushed through the vessel, point 182 is proximal of the point 184. Regardless of the direction of movement of the instrument, the instrument will cross one or more lesions and/or stenosis of the vessel between the point 182 and the point 184. In that regard, each of the visual depictions of FIGS. 5-8 is configured to identify the one or more lesions and/or stenosis based on pressure measurements obtained from the instrument as the instrument is moved through the vessel.

Referring again to FIG. 5, visual representation 180 is a heat map that illustrates changes in pressure measurements obtained as the instrument is moved through the vessel. In that regard, in some instances the pressure measurements shown in the heat map are representative of a pressure differential between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer the fixed position of the distal pressure measurement). For clarity in understanding the concepts of the present disclosure, this arrangement will be utilized to describe many of the embodiments of the present disclosure. However, it is understood that the concepts are equally applicable to other arrangements. For example, in some instances, the instrument is pushed through the vessel from a first position distal of the proximal pressure measurement location to a second position further distal (i.e., further away from the fixed position of the proximal pressure measurement). In other instances, a distal pressure measurement is obtained at a fixed location within the vessel and the instrument is pulled back through the vessel from a first position proximal of the fixed location of the distal pressure measurement to a second position more proximal than the first position (i.e., further away from the fixed position of the distal pressure measurement). In still other instances, a distal pressure measurement is obtained at a fixed location within the vessel and the instrument is pushed through the vessel from a first position proximal of the fixed location of the distal pressure measurement to a second position less proximal than the first position (i.e., closer the fixed position of the distal pressure measurement).

The pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances. In some instances, the pressure differential is calculated for each heartbeat cycle of the patient. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances. In that regard, in some embodiments a diagnostic window is selected using one or more of the techniques described in U.S. Patent Application No. 61/525,739, now U.S. Nonprovisional patent application Ser. No. 13/460,296 filed Apr. 30, 2012, which is hereby incorporated by reference in its entirety. As discussed therein, the diagnostic windows and associated techniques of U.S. Patent Application No. 61/525,739, now U.S. Nonprovisional patent application Ser. No. 13/460,296 filed Apr. 30, 2012, are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

In some embodiments, the determination of the diagnostic window and/or the calculation of the pressure differential are performed in approximately real time or live to identify the section 212 and calculate the pressure differential. In that regard, calculating the pressure differential in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure differential calculation is performed 10 or more seconds after data acquisition. For example, in some embodiments, the data utilized to identify the diagnostic window and/or calculate the pressure differential are stored for later analysis.

By comparing the calculated pressure differential to a threshold or predetermined value, a physician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

In that regard, the coloring and/or other visually distinguishing aspect of the pressure differential measurements depicted in visual representation 180 of FIG. 5 are configured based on the threshold value. For example, a first color (e.g., green, white, or otherwise) is utilized to represent values well above the threshold value (e.g., where the threshold value is 0.80 on a scale of 0.00 to 1.00, values above 0.90), a second color (e.g., yellow, gray, or otherwise) is utilized to represent values near but above the threshold value (e.g., where the threshold value is 0.80 on a scale of 0.00 to 1.00, values between 0.81 and 0.90), and a third color (e.g., red, black, or otherwise) is utilized to represent values equal to or below the threshold value (e.g., where the threshold value is 0.80 on a scale of 0.00 to 1.00, values of 0.80 and below). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

As shown in FIG. 5, the heat map of visual representation 180 utilizes a gray scale where lighter or whiter colors are representative of values above the threshold value, while darker or blacker colors are representative of values near or below the threshold value. In that regard, the heat map of visual representation 180 is based on a cumulative or total pressure differential, where the gray scale color selected for a particular point is determined based on the pressure differential between the instrument at that point being moved through the vessel and the stationary or fixed instrument. As shown, in the illustrated embodiment a transition point or area 186 of the vessel is positioned between a portion 188 of the vessel having pressure differential values above the threshold value and a portion 190 of the vessel having pressure differential values below the threshold value. In that regard, the transition point or area 186 is representative of a boundary of a lesion or stenosis of the vessel that results in an increased pressure differential, which is illustrated by the change in color of the visual representation 180. As a result, the visual representation 180 can be utilized to both identify the location of the lesion or stenosis within the vessel and assess the severity of the lesion or stenosis.

Figure 6:
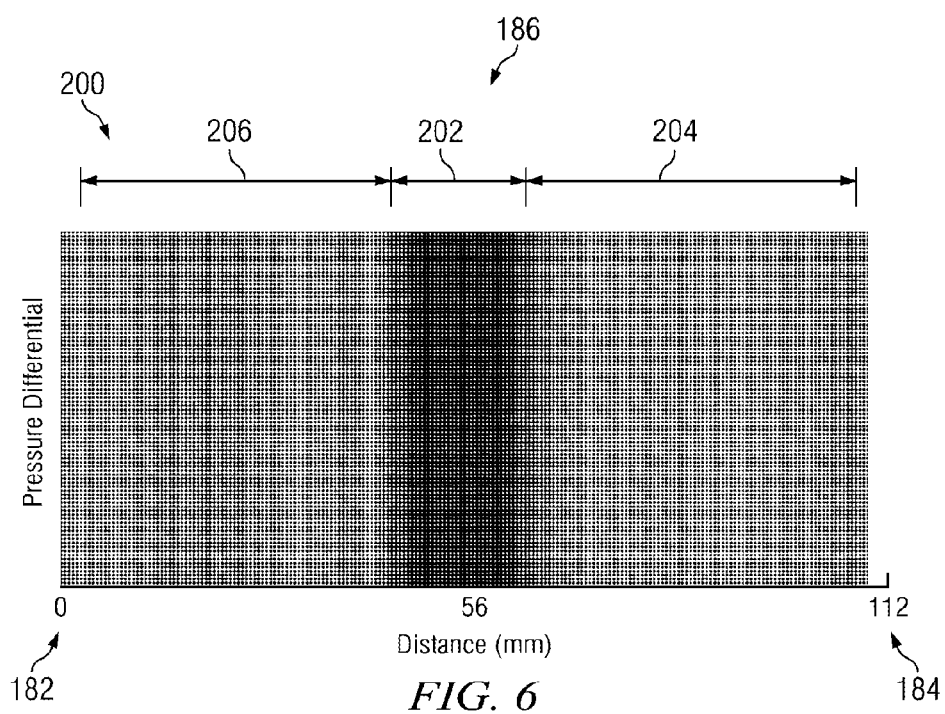
FIG. 6 is a visual depiction of a vessel profile based on pressure measurements similar to that of FIG. 5, but illustrating an alternative embodiment of the present disclosure.

Referring now to FIG. 6, shown therein is a visual representation 200 of a vessel profile based on the same pressure measurements as the visual representation 180 of FIG. 5. In that regard, the heat map of visual representation 200 also utilizes a gray scale where lighter or whiter colors are representative of values above a threshold value, while darker or blacker colors are representative of values near or below the threshold value. While the heat map of visual representation 180 was based on a cumulative or total pressure differential, the heat map of visual representation 200 is based on a localized pressure differential, where the gray scale color selected for a particular point is determined based on differences between the pressure differential of that point with one or more of the surrounding points. In that regard, the localized pressure differential is calculated as the difference between the immediately preceding point in some instances. For example, the localized pressure differential for point Pn is equal to the cumulative or total pressure differential for point Pn minus the total or cumulative pressure differential for point Pn−1. In other instances, the localized pressure differential is calculated as the difference between that point and a point a fixed amount of time (e.g., 10 ms, 5 ms, 2 ms, 1 ms, or otherwise) or distance (e.g., 10 mm, 5 mm, 2 mm, 1 mm, or otherwise) away from that point. By utilizing a localized pressure differential the location of significant changes in pressure differential values, which are often associated with the presence of a lesion or stenosis, can be identified.

For example, as shown in the illustrated embodiment of FIG. 6, a transition area 202 of the vessel having localized pressure differential values below the threshold is positioned between portions 204 and 206 of the vessel having pressure differential values above the threshold value. In that regard, the transition point or area 202 is representative of a lesion or stenosis of the vessel that results in a significant change in pressure differential, which is illustrated by the change in color of the visual representation 200. As a result, the visual representation 200 can be utilized to both identify the location of the lesion or stenosis within the vessel and assess the severity of the lesion or stenosis.

Figure 7:
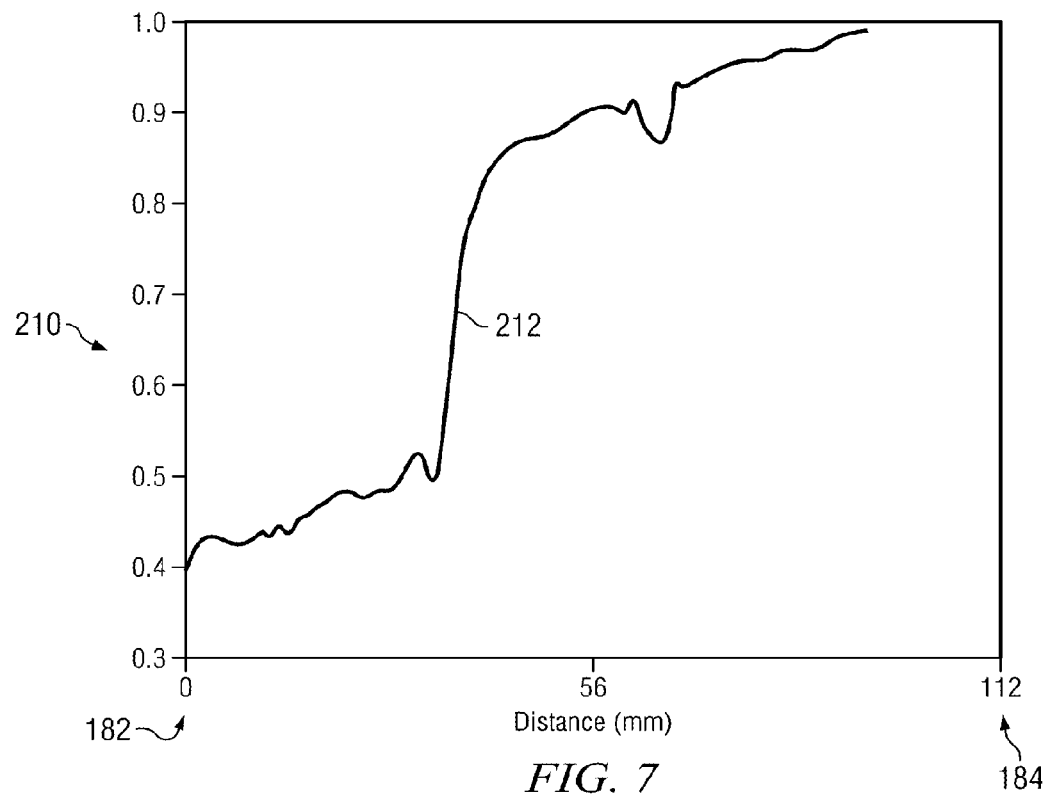
FIG. 7 is a visual depiction of a vessel profile based on pressure measurements according to another embodiment of the present disclosure.

Referring now to FIG. 7, shown therein is a visual representation 210 of a vessel profile based on the same pressure measurements as the visual representations 180 and 200 of FIGS. 5 and 6, respectively. In that regard, FIG. 7 illustrates a plot 212 of the cumulative or total pressure differential between the instrument being moved through the vessel and an instrument at a stationary or fixed position within the vessel. By analyzing the shape of the plot 212 and, in particular, such characteristics as the pressure differential value relative to the threshold value, changes in the slope of the plot, and/or combinations thereof, the visual representation 210 can be utilized to both identify the location of the lesion or stenosis within the vessel and assess the severity of the lesion or stenosis.

Figure 8:
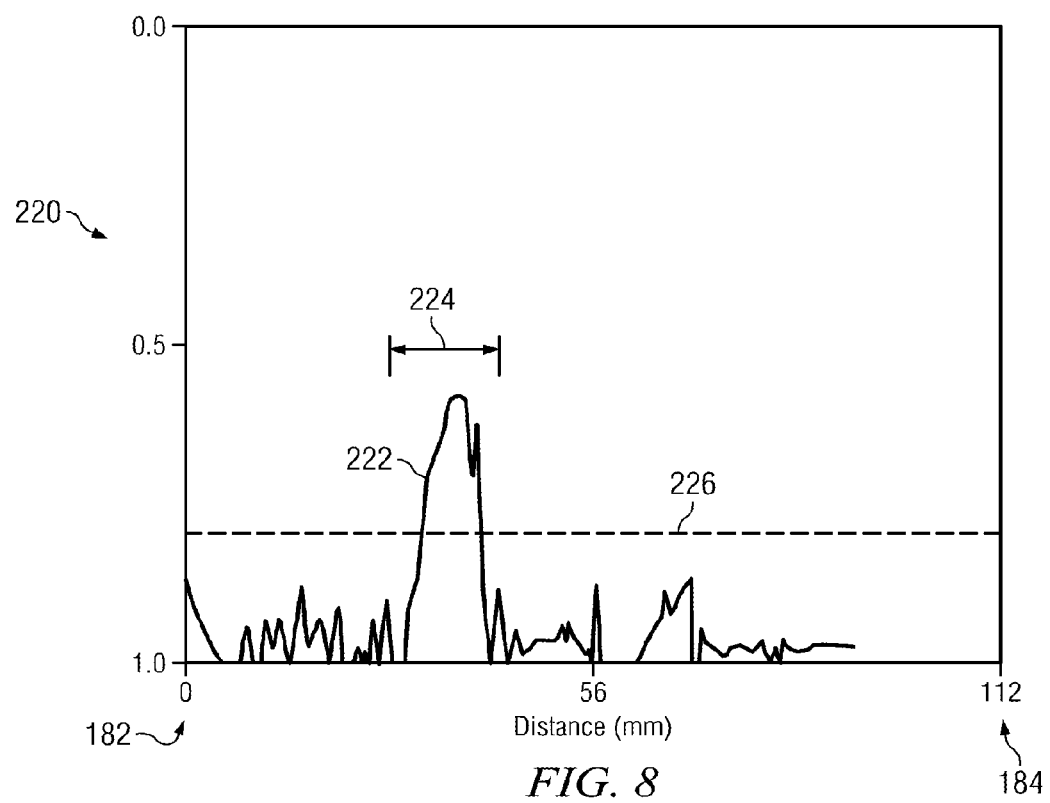
FIG. 8 is a visual depiction of a vessel profile based on pressure measurements according to another embodiment of the present disclosure.

Referring now to FIG. 8, shown therein is a visual representation 220 of a vessel profile based on the same pressure measurements as the visual representations 180, 200, and 210 of FIGS. 5, 6, and 7, respectively. In that regard, FIG. 8 illustrates a plot 222 that is based on differences between the pressure differential of a point with one or more of the surrounding points. In that regard, the values utilized for plot 222 are calculated as the difference between adjacent points in some instances. For example, the value for point Pn is equal to the cumulative or total pressure differential for point Pn minus the total or cumulative pressure differential for point Pn−1, in some instances. In other instances, the value utilized a particular point of plot 222 is calculated as the difference between the pressure differential for that point and another point a fixed amount of time (e.g., 10 ms, 5 ms, 2 ms, 1 ms, or otherwise) or distance (e.g., 10 mm, 5 mm, 2 mm, 1 mm, or otherwise) away from that point. In the illustrated embodiment, plot 222 is based upon the differences in pressure differential between points 2 mm apart from one another. Utilizing these relative and localized calculations of pressure differential, the location of significant changes in pressure differential values that are associated with the presence of a lesion or stenosis can be identified.

The plot 222 can be utilized to both identify the location of lesions or stenosis within the vessel as well as assess the severity of the identified lesions or stenosis. In the illustrated embodiment of FIG. 8, a region 224 of the plot 222 does not meet the threshold value indicated by line 226. In that regard, it should be noted that in FIG. 8, the y-axis values of the visual representation 220 go from 1.0 at the origin to 0.0 at the top of the illustrated y-axis. Accordingly, region 224 represents a lesion or stenosis of the vessel that is adversely impacting fluid flow to a degree that requires treatment. Analysis of the plot 222 provides information about the vessel and/or its lesions or stenosis. For example, the plot 222 provides an indication of the length of the lesion or stenosis associated with region 224. In that regard, the length of the lesion or stenosis is indicated by the length of the vessel segment having values less than the threshold value 226. In the illustrated embodiment, the length of the vessel segment having values less than the threshold value 226 is approximately 17 mm. The length of the lesion or stenosis as indicated by the plot 222 is based entirely on physiologic measurements that are independent of lesion composition.

Further, the plot 222 provides an indication of the overall occlusive value of the vessel. In that regard, the total vessel occlusive value is determined by cumulative area under the plot 222 in some instance. In the illustrated embodiment, the total vessel occlusive value or area under the plot 222 is approximately 1.38. Similarly, the plot 222 also provides an indication of the occlusive value attributable to individual lesions or stenosis of the vessel. In that regard, the occlusive value attributable to a particular lesion or stenosis can similarly be calculated by determining the area under the plot 222 for a length of the vessel associated with the lesion or stenosis. For example, in the illustrated embodiment the lesion or stenosis associated with region 224 has an occlusive value or area under the plot 222 of approximately 0.67. Based on the total vessel occlusive value and the occlusive value attributable to a particular lesion or stenosis, a percentage of the total vessel occlusive value attributable to that particular lesion or stenosis can be calculated. In that regard, the ratio of the occlusive value attributable to the particular lesion or stenosis to the total occlusive value of the vessel provides the percentage of vessel occlusion attributable to that lesion or stenosis. The information regarding characteristics of the lesion or stenosis and/or the vessel as indicated by the plot 222 can be compared with or considered in addition to other representations of the lesion or stenosis and/or the vessel (e.g., IVUS (including virtual histology), OCT, ICE, Thermal, Infrared, flow, Doppler flow, and/or other vessel data-gathering modalities) to provide a more complete and/or accurate understanding of the vessel characteristics. For example, in some instances the information regarding characteristics of the lesion or stenosis and/or the vessel as indicated by the plot 222 are utilized to confirm information calculated or determined using one or more other vessel data-gathering modalities.

While the visual representations 180, 200, 210, and 220 of FIGS. 5, 6, 7, and 8 have been described separately. It is understood that a system may display any combination of these visual representations in series, simultaneously, and/or combinations thereof. In some instances, a system provides the user the ability to select which individual visual representation and/or combination of visual representations will be displayed.

Figure 9:
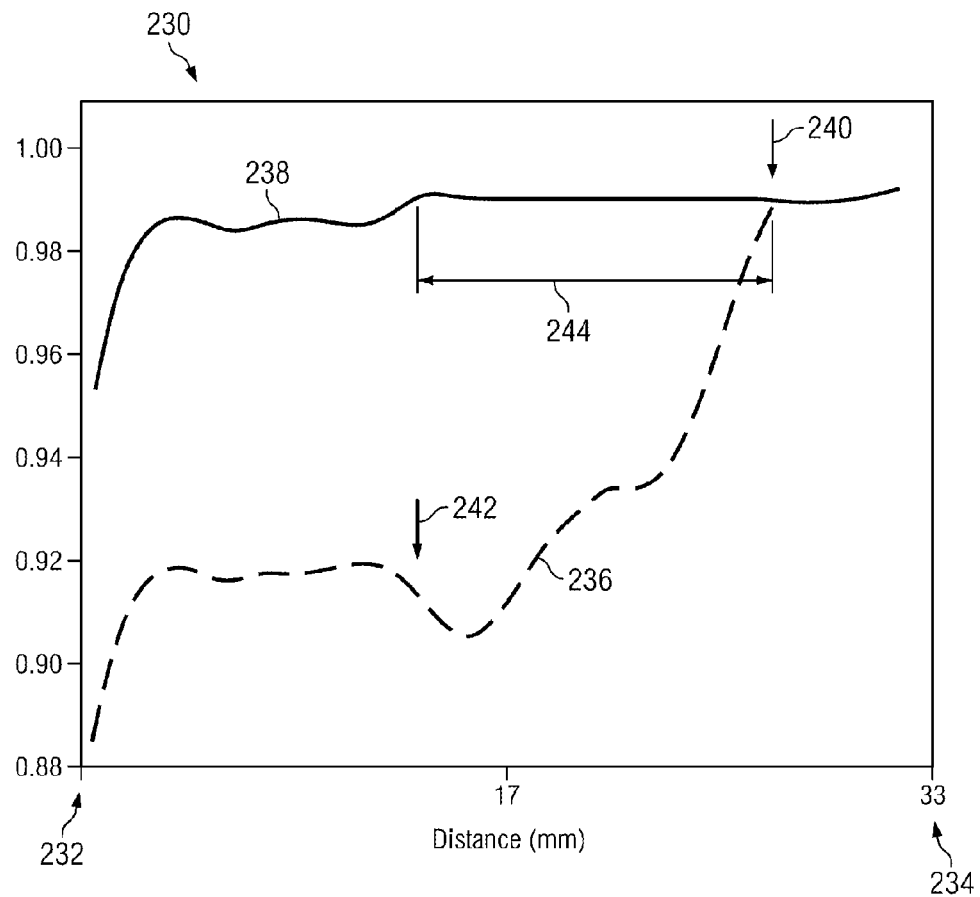
FIG. 9 is a visual depiction of a vessel illustrating a simulated treatment option according to an embodiment of the present disclosure.

Referring now to FIG. 9, shown therein is a visual representation 230 of a vessel illustrating a simulated treatment option according to an embodiment of the present disclosure. In that regard, visual representation 230 illustrates approximately a 33 mm segment of the vessel between points 232 and 234. In that regard, point 232 is representative of a starting position of an instrument within the vessel while point 234 is representative of an ending position of the instrument within the vessel after movement of the instrument longitudinally along the lumen of the vessel. Accordingly, in the instance of a pullback of the instrument, point 232 is distal of point 234 within the vessel. On the other hand, in the instance where the instrument pushed through the vessel, point 232 is proximal of the point 234. Regardless of the direction of movement of the instrument, the instrument will cross one or more lesions and/or stenosis of the vessel between the point 232 and the point 234. In that regard, visual representation 230 includes a plot 236 of the cumulative or total pressure differential between the instrument being moved through the vessel and an instrument at a stationary or fixed position within the vessel. By analyzing the shape of the plot 236 and, in particular, such characteristics as the pressure differential value relative to the threshold value, changes in the slope of the plot, and/or combinations thereof, the visual representation 230 can be utilized to both identify the location of the lesion or stenosis within the vessel and assess the severity of the lesion or stenosis.

Based on information about the lesion or stenosis derived from visual representation 230, one or more treatment options (e.g., angioplasty, stent(s), pharmaceutical(s), etc.) can be simulated. For example, plot 238 is representative of one treatment option for the vessel. In that regard, based on the characteristics of the plot 232 two opposing ends 240, 242 of a lesion or stenosis are identified. In some instances, the ends 240, 242 are identified based on changes in slope of the plot 232. In other instances, the ends are identified using one or more of the imaging and/or analysis techniques discussed above with respect to FIGS. 5-8. The two ends 240, 242 define a region 244 associated with the lesion or stenosis. As a result, the region 244 also corresponds to the treatment region. Accordingly, in some embodiments a treatment option is simulated by adjusting the values of the plot 236 to be representative of the expected outcome of that treatment option across region 244, which are graphed a part of plot 238. In that regard, the expected outcome can be selected by a user, based on parameters selected by the user, based on characteristics of the patient, based on empirical data, and/or combinations thereof. For example, in some instances, the system is in communication with one or more databases containing empirical data regarding the results of treatment options for patients having various characteristics. Accordingly, in some instances the adjusted values of graph 238 are determined based on such factors as patient age, patient gender, patient medical history (e.g., previous treatments, previous cardiac events, etc.), vessel characteristics, lesion or stenosis characteristics, and/or other information relevant for treatment of the patient. In some instances, where the calculated pressure differential (either total or localized) is compared to a threshold or predetermined value, the simulated plot of the treatment option adjusts the pressure differential values to meet the threshold. For example, where the threshold value is 0.80 on a scale of 0.00 to 1.00, then the viable treatment options will have values between about 0.90 and about 1.00 on the simulated plot in some instances.

With the plot 238 representing the expected outcome of the treatment option a user or medical personnel can determine whether the treatment option is viable approach. By simulating and evaluating a plurality of treatment options, the user or medical personnel can select the most promising treatment approach for the patient. In some instances, plots of multiple simulated treatment are displayed simultaneously on the visual representation 230 (e.g., using different colors for each treatment) to allow a user to compare the treatment options. In that regard, the user or medical personnel selects the treatment options to be shown and considered in some instances. Further, in some instances each of the treatment options can be analyzed objectively using one or more computational techniques based on the simulated plot and compared to one another. For example, calculations such as total vessel occlusive value, lesion or stenosis occlusive value, and/or lesion or stenosis occlusive percentage, as discussed above with respect to FIG. 8, are utilized to evaluate the treatment options in some instances.

Figure 10:
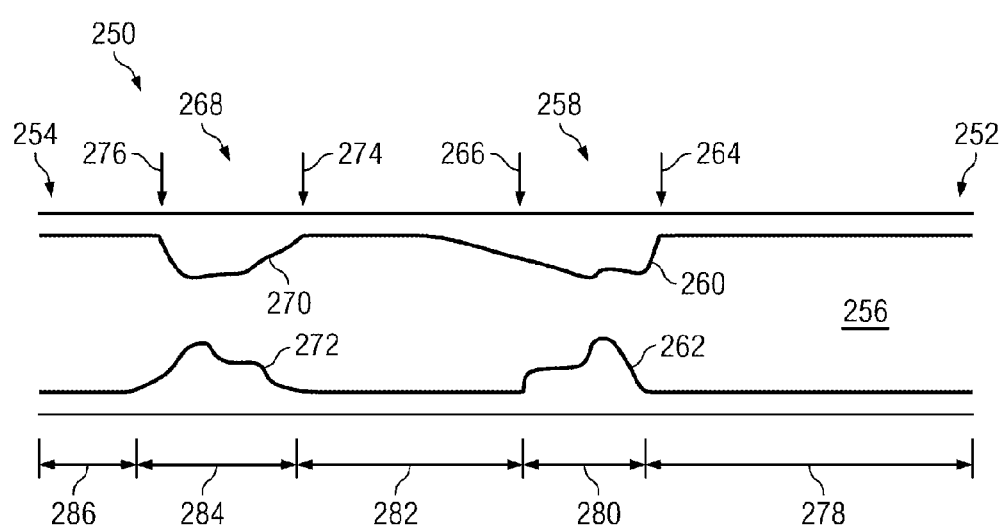
FIG. 10 is a cross-sectional side view of a vessel according to an embodiment of the present disclosure.
Figure 11:
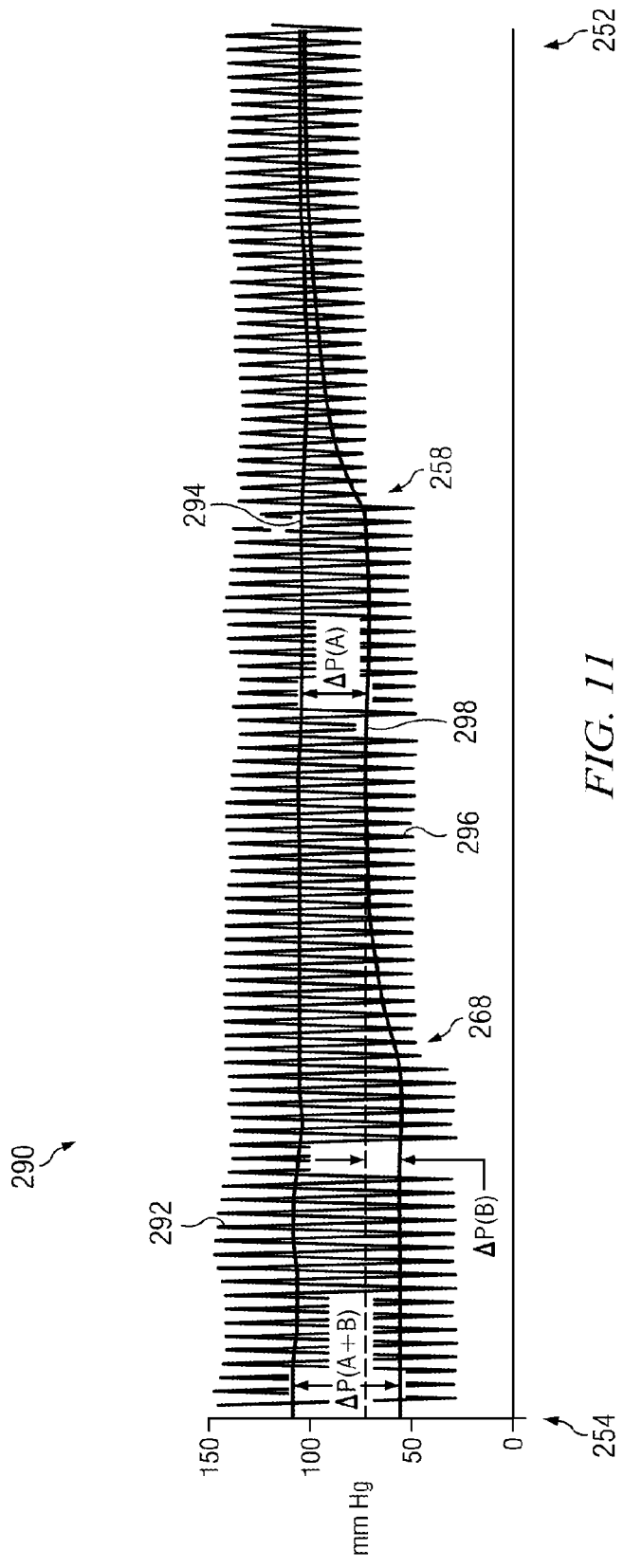
FIG. 11 is a graphical representation of pressure measurements obtained from within the vessel of FIG. 10 according to an embodiment of the present disclosure.
Figure 12:
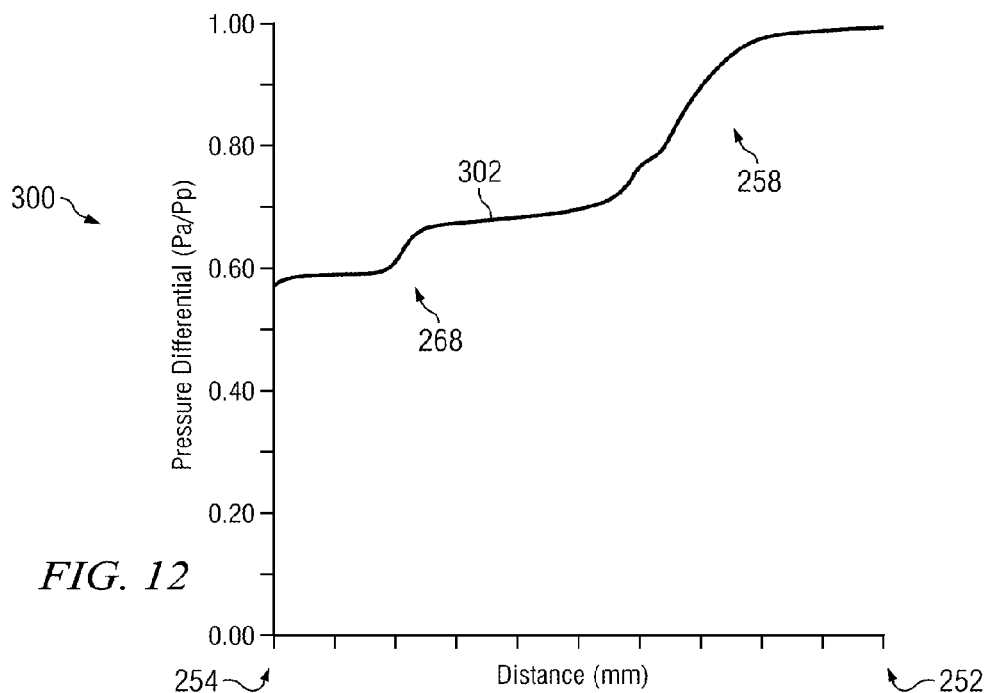
FIG. 12 is a visual depiction of the vessel of FIG. 10 based on the pressure measurements of FIG. 11 according to an embodiment of the present disclosure.
Figure 13:
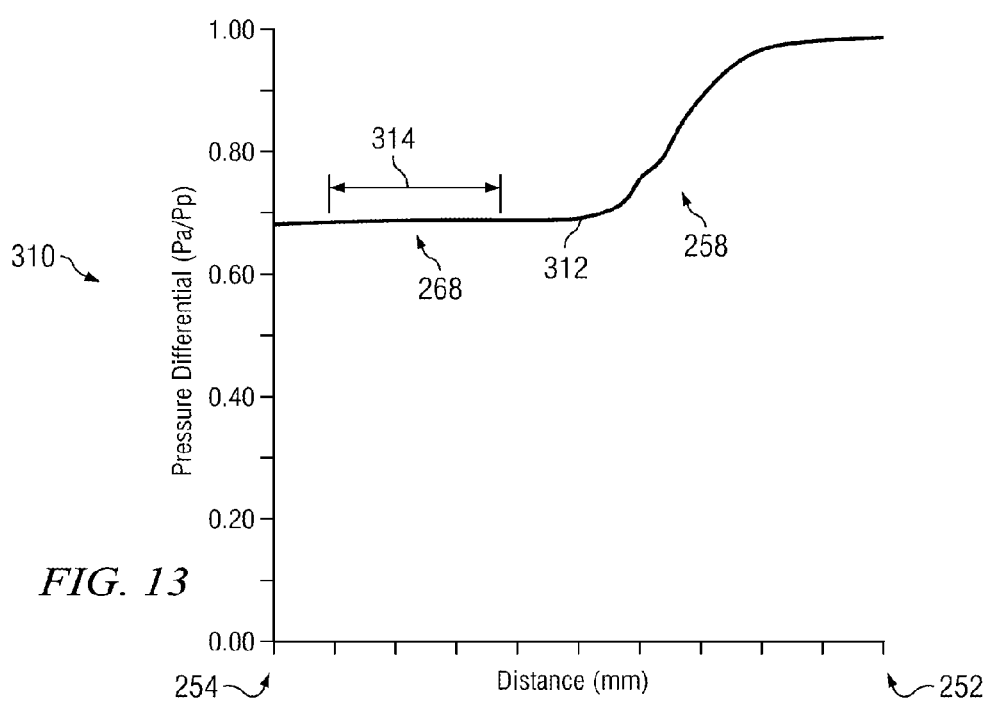
FIG. 13 is a visual depiction of the vessel of FIG. 10, similar to that of FIG. 12, but illustrating a first simulated treatment option.
Figure 14:
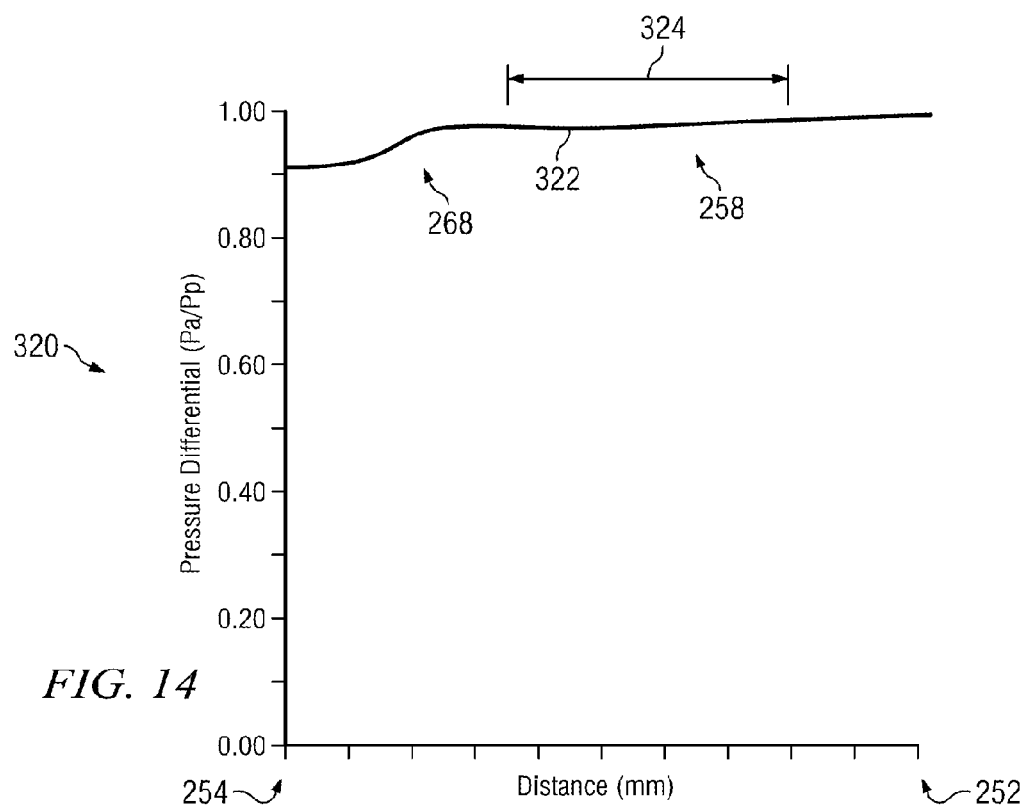
FIG. 14 is a visual depiction of the vessel of FIG. 10, similar to that of FIGS. 12 and 13, but illustrating a second simulated treatment option.
Figure 15:
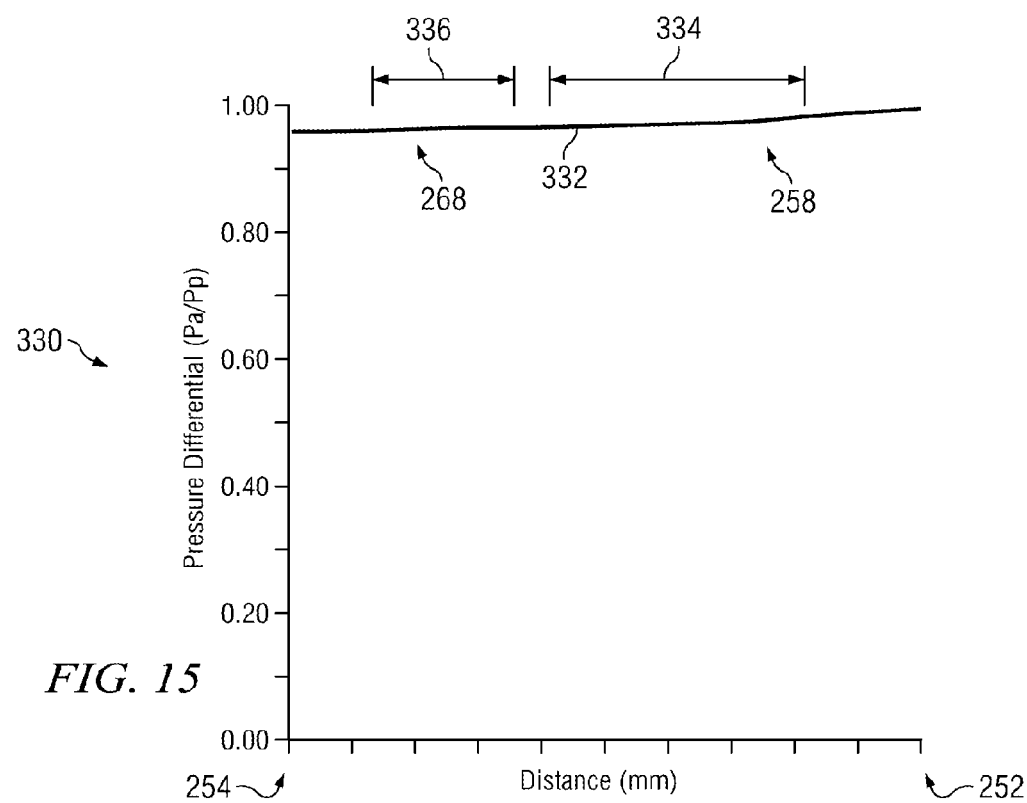
FIG. 15 is a visual depiction of the vessel of FIG. 10, similar to that of FIGS. 12-14, but illustrating a third simulated treatment option.

Referring now to FIGS. 10-15, shown therein are aspects of the present disclosure related to vessels having multiple lesions or stenosis. In that regard, FIG. 10 is a cross-sectional side view of a vessel having two lesions or two stenosis according to an embodiment of the present disclosure; FIG. 11 is a graphical representation of pressure measurements obtained from within the vessel of FIG. 10; FIG. 12 is a visual depiction of the vessel of FIG. 10 based on the pressure measurements of FIG. 11; FIG. 13 is a visual depiction of the vessel illustrating a first simulated treatment option; FIG. 14 is a visual depiction of the vessel illustrating a second simulated treatment option; and FIG. 15 is a visual depiction of the vessel illustrating a third simulated treatment option.

Referring more specifically to FIG. 10, shown therein is a vessel 250 according to an embodiment of the present disclosure. The vessel 250 includes a proximal portion 252 and a distal portion 254. A lumen 256 extends longitudinally along the length of the vessel 250 between the proximal portion 252 and the distal portion 254. The vessel 250 also includes a stenosis 258 having an upper portion 260 and a lower portion 262. In that regard, the upper and lower portions 260, 262 are representative of plaque buildup that narrows the lumen 256 of the vessel 250. In some instances, the plaque buildup of the stenosis 258 does not have a uniform or symmetrical profile, making angiographic evaluation of such a stenosis unreliable. As shown, the stenosis 258 decreases the available space for fluid to flow through the lumen 256. In particular, the cross-sectional area of the lumen 256 is decreased by the stenosis 258. The stenosis 258 also has a proximal boundary 264 and a distal boundary 266. It should be noted that the proximal and/or distal boundaries of the upper and lower portions 260, 262 are not aligned in all instances. For example, in the illustrated embodiment the upper portion 260 tapers slowly as it extends distally, while lower portion 262 comes to a more abrupt end. In such instances, these characteristics can be taken into account when determining the boundary of the stenosis 258 as a whole. Stenosis 258 is exemplary in nature and should not be considered limiting in any way. In that regard, it is understood that the stenosis 258 has other shapes and/or compositions that limit the flow of fluid through the lumen 256 in other instances.

The vessel 250 also includes a stenosis 268 having an upper portion 270 and a lower portion 272. In that regard, the upper and lower portions 270, 272 are representative of plaque buildup that narrows the lumen 256 of the vessel 250. In some instances, the plaque buildup of the stenosis 268 does not have a uniform or symmetrical profile, making angiographic evaluation of such a stenosis unreliable. As shown, the stenosis 268 decreases the available space for fluid to flow through the lumen 256. In particular, the cross-sectional area of the lumen 256 is decreased by the stenosis 268. The stenosis 268 also has a proximal boundary 274 and a distal boundary 276. It should be noted that the proximal and/or distal boundaries of the upper and lower portions 270, 272 are not aligned in all instances. Stenosis 268 is exemplary in nature and should not be considered limiting in any way. In that regard, it is understood that the stenosis 268 has other shapes and/or compositions that limit the flow of fluid through the lumen 256 in other instances.

Based on the presence of stenosis 258 and 268, the vessel 250 can be divided into five regions. Namely, region 278 located proximal of stenosis 258, region 280 located between the proximal and distal boundaries 264, 266 of stenosis 258, region 282 located between stenosis 258 and stenosis 268, region 284 located between the proximal and distal boundaries 274, 276 of stenosis 268, and region 286 located distal of stenosis 268.

Referring now to FIG. 11, shown therein is a graphical representation 290 of pressure measurements obtained from within the vessel 250 of FIG. 10. In that regard, the graphical representation 290 includes a proximal pressure measurement graph 292 that is representative of pressure measurements obtained at a position proximal of the stenosis 258 (i.e., within region 278). An average of the proximal pressure measurement graph 292 is represented by average line 294. The graphical representation 290 also includes a distal pressure measurement graph 292 that is representative of pressure measurements obtained at a distal of the position where the proximal pressure measurements are obtained. In particular, the distal pressure measurement graph 296 is representative of a pullback of instrument from a position distal of stenosis 268 (i.e., within region 286) across stenosis 268 and stenosis 258 to a position proximal of stenosis 258 (i.e., within region 278). An average of the distal pressure measurement graph 296 is represented by average line 298. As shown, the pressure differential between the proximal and distal pressure measurements decreases as the instrument utilized for obtaining the distal pressure measurements is moved proximally across stenosis 268 and stenosis 258 towards the instrument utilized for obtaining the proximal pressure measurements. In that regard, FIG. 12 provides a visual representation 300 of the vessel 250 based on the pressure measurements of FIG. 11. In particular, visual representation 300 includes a plot 302 of the pressure differential between the proximal and distal pressure measurements along the length of the vessel between the distal and proximal portions 254, 252. In that regard, plot 302 is representative of a total pressure differential. However, in other embodiments a localized pressure differential is utilized.

Based on information about stenosis 258, stenosis 268, and/or vessel 250 derived from visual representation 300, one or more treatment options (e.g., angioplasty, stent(s), pharmaceutical(s), etc.) can be simulated for the vessel 250. In that regard, the techniques discussed above with respect to FIG. 9 for simulating and/or evaluating treatment options for a vessel having a single lesion or stenosis can likewise be applied to vessels having multiple lesions or stenosis, as with vessel 250. FIGS. 13-15 illustrate three different treatment options for vessel 250 in accordance with embodiments of the present disclosure.

Referring now to FIG. 13, shown therein is a visual representation 310 of the vessel 250 illustrating a first simulated treatment option for vessel 250. In that regard, visual representation 310 includes a plot 312 of estimated pressure differentials through the vessel 250 based upon the plot 302 and the expected results of the first treatment option. More specifically, the visual representation 310 illustrates a treatment option where stenosis 268 is treated, but stenosis 258 is not treated. Accordingly, the values of the plot 312 associated with a region 314 corresponding to the treatment region have been adjusted to reflect the expected results of the treating the stenosis 268. The remaining values of the plot 312 are adjusted, as necessary, to fit with the adjusted values of region 314. As shown, with treatment of stenosis 268 alone, the vessel 250 includes a drop in pressure differential around stenosis 258. In that regard, if the threshold pressure differential for vessel 250 is 0.80 on a scale of 0.00 to 1.00, then the first treatment option associated with plot 312 is not a viable treatment option due to the drop in pressure differential values to approximately 0.65 around stenosis 258.

Referring now to FIG. 14, shown therein is a visual representation 320 of the vessel 250 illustrating a second simulated treatment option for vessel 250. In that regard, visual representation 320 includes a plot 322 of estimated pressure differentials through the vessel 250 based upon the plot 302 and the expected results of the second treatment option. More specifically, the visual representation 320 illustrates a treatment option where stenosis 258 is treated, but stenosis 268 is not treated. Accordingly, the values of the plot 322 associated with a region 324 corresponding to the treatment region have been adjusted to reflect the expected results of the treating the stenosis 258. The remaining values of the plot 322 are adjusted, as necessary, to fit with the adjusted values of region 324. As shown, with treatment of stenosis 258 alone, the vessel 250 includes a drop in pressure differential around stenosis 268. In that regard, if the threshold pressure differential for vessel 250 is 0.80 on a scale of 0.00 to 1.00, then the second treatment option associated with plot 322 is a viable treatment option because the drop in pressure differential values to approximately 0.92 around stenosis 268 is still well above the threshold.

Referring now to FIG. 15, shown therein is a visual representation 330 of the vessel 250 illustrating a third simulated treatment option for vessel 250. In that regard, visual representation 330 includes a plot 332 of estimated pressure differentials through the vessel 250 based upon the plot 302 and the expected results of the third treatment option. More specifically, the visual representation 330 illustrates a treatment option where both stenosis 258 and stenosis 268 are treated. Accordingly, the values of the plot 332 associated with a region 334 corresponding to the treatment region of stenosis 258 have been adjusted to reflect the expected results of the treating the stenosis 258, while the values of the plot 332 associated with a region 336 corresponding to the treatment region of stenosis 268 have been adjusted to reflect the expected results of the treating the stenosis 268. The remaining values of the plot 332 are adjusted, as necessary, to fit with the adjusted values of regions 334 and 336. As shown, with treatment of both stenosis 258 and stenosis 268, the vessel 250 has a relatively constant pressure differential from the proximal portion 252 to the distal portion 254. In that regard, if the threshold pressure differential for vessel 250 is 0.80 on a scale of 0.00 to 1.00, then the third treatment option associated with plot 332 is a viable treatment option because the slight drops in pressure differential values to approximately 0.98 at various points along the length of the vessel is well above the threshold.

With the visual representations 310, 320, and 330 representing the expected outcomes of the three treatment options a user or medical personnel can determine which of the treatment options is the most viable approach. For example, the user or medical personnel may select the second treatment option (visual representation 320) because the treatment meets the threshold requirements and requires treatment of only stenosis 258, which can save both time and money. On the other hand, a user or medical personnel may select the third treatment option (visual representation 330) because of the overall improvement in pressure differential throughout the vessel compared to the second treatment option. By simulating and evaluating a plurality of treatment options, the user or medical personnel can select the most beneficial treatment approach for the patient. In some instances, plots of multiple simulated treatment are displayed to the user or medical personnel simultaneously (e.g., using different colors on one graph and/or displayed on separated graphs adjacent to one another) to allow the user or medical personnel to compare the treatment options. Again, in some instances the treatment options are analyzed objectively using one or more computational techniques based on the simulated plot and compared to one another.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of evaluating a vessel of a patient, comprising:
    introducing a first instrument into the vessel of the patient;
    introducing a second instrument into the vessel of the patient;
    moving the second instrument longitudinally through the vessel of the patient from a first position to a second position while maintaining the first instrument in a fixed longitudinal position with respect to the vessel;
    obtaining pressure measurements from the first and second instruments while the second instrument is moved longitudinally through the vessel;
    calculating pressure ratios of the pressure measurements obtained by the second instrument to the pressure measurements obtained by the first instrument;
    visually depicting the pressure ratios on a display, wherein the visual depiction of the pressure ratios comprises a graph including a graphical representation of the pressure ratios; and
    modifying the graph to simulate one or more treatment options, wherein modifying the graph comprises changing a shape of the graphical representation in the graph to simulate an increase in the pressure ratios resulting from the one or more treatment options.

2. The method of claim 1, wherein the first position is distal of at least one stenosis of the vessel.

3. The method of claim 2, wherein the second position is proximal of the at least one stenosis of the vessel such that moving the second instrument longitudinally through the vessel comprises a pullback.

4. The method of claim 1, wherein the first position is proximal of at least one stenosis of the vessel.

5. The method of claim 4, wherein the second position is distal of the at least one stenosis of the vessel.

6. The method of claim 1, wherein modifying the graph to simulate one or more treatment options comprises:
modifying the graph to simulate a first treatment option;
modifying the graph to simulate a second treatment option; and
evaluating the modified graphs to select either the first treatment option or the second treatment option.

7. The method of claim 6, further comprising performing the selected treatment option.

8. The method of claim 1, wherein the one or more treatment options are selected from the group of treatment options consisting of: an angioplasty, a stent, a pharmaceutical, and combinations thereof.

9. The method of claim 1, wherein the pressure ratios are calculated by dividing the pressure measurements obtained from the second instrument by the pressure measurements obtained from the first instrument.

10. The method of claim 1, wherein visually depicting the pressure ratios includes graphing a total pressure differential between pressure measurements obtained from the first instrument and the pressure measurements obtained from the second instrument.

11. The method of claim 1, wherein visually depicting the pressure ratios includes graphing a localized pressure differential between pressure measurements obtained from the first instrument and the pressure measurements obtained from the second instrument.

12. The method of claim 11, wherein the localized pressure differentials are calculated based on points separated by a fixed amount of time.

13. The method of claim 11, wherein the localized pressure differentials are calculated based on points separated by a fixed length.

14. The method of claim 1, further comprising evaluating the one or more treatment options based on the modified graph.

15. The method of claim 14, wherein evaluating the one or more treatment options comprises determining whether the modified graph satisfies a predetermined requirement.

16. The method of claim 15, wherein the predetermined requirement is a threshold pressure differential.

17. The method of claim 16, wherein the threshold pressure differential is 0.80.

18. The method of claim 15, further comprising performing at least one of the one or more treatment options that satisfies the predetermined requirement.

19. The method of claim 18, wherein the at least one treatment option that is performed is selected from the group of treatment options consisting of: an angioplasty, a stent, a pharmaceutical, and combinations thereof.

20. A system for evaluating a vessel of a patient, comprising:
a first instrument sized and shaped for introduction into the vessel of the patient;
a second instrument sized and shaped for introduction into the vessel of the patient;
a processing unit in communication with the first and second instruments, the processing unit configured to:
obtain pressure measurements from the first and second instruments while the second instrument is moved longitudinally through the vessel of the patient from a first position to a second position while the first instrument is maintained in a fixed longitudinal position with respect to the vessel;
calculate pressure ratios of the pressure measurements obtained by the second instrument to the pressure measurements obtained by the first instrument;
visually depict the pressure ratios on a display, wherein the visual depiction of the pressure ratios comprises a graph including a graphical representation of the pressure ratios; and
modify the graph to simulate one or more treatment options, wherein modifying the graph comprises changing a shape of the graphical representation in the graph to simulate an increase in the pressure ratios resulting from the one or more treatment options.

21. A method of evaluating a vessel of a patient, comprising:
introducing an instrument into the vessel of the patient;
moving the instrument longitudinally through the vessel of the patient from a first position to a second position;
obtaining pressure measurements from the instrument at a plurality of positions along the vessel as the instrument is moved longitudinally through the vessel;
calculating pressure ratios of the pressure measurements obtained by the instrument;
visually depicting the pressure ratios on a display, wherein the visual depiction of the pressure ratios comprises a graph including a graphical representation of the pressure ratios; and
modifying the graph to simulate one or more treatment options, wherein modifying the graph comprises changing a shape of the graphical representation in the graph to simulate an increase in the pressure ratios resulting from the one or more treatment options.

22. The method of claim 21, wherein the first position is distal of at least one stenosis of the vessel.

23. The method of claim 22, wherein the second position is proximal of the at least one stenosis of the vessel such that moving the instrument longitudinally through the vessel comprises a pullback.

24. The method of claim 21, wherein the first position is proximal of at least one stenosis of the vessel.

25. The method of claim 24, wherein the second position is distal of the at least one stenosis of the vessel.

26. The method of claim 21, wherein modifying the graph to simulate one or more treatment options comprises:
modifying the graph to simulate a first treatment option;
modifying the graph to simulate a second treatment option; and
evaluating the modified graphs to select either the first treatment option or the second treatment option.

27. The method of claim 26, further comprising performing the selected treatment option.

28. The method of claim 21, wherein the one or more treatment options are selected from the group of treatment options consisting of an angioplasty, a stent, a pharmaceutical, and combinations thereof.

29. The method of claim 21, wherein visually depicting the pressure ratios comprises graphing pressure differentials between sequential pressure measurements obtained from the instrument.

30. The method of claim 29, wherein the sequential pressure measurements are separated by a fixed amount of time.

31. The method of claim 30, wherein the sequential pressure measurements are separated by a fixed number of pressure measurements obtained from the instrument.

32. The method of claim 21, further comprising evaluating the one or more treatment options based on the modified graph.

33. The method of claim 32, wherein evaluating the one or more treatment options comprises determining whether the modified graph satisfies a predetermined requirement.

34. The method of claim 33, wherein the predetermined requirement is a threshold pressure differential.

35. The method of claim 34, wherein the threshold pressure differential is 0.80.

36. The method of claim 33, further comprising performing at least one of the one or more treatment options that satisfies the predetermined requirement.

37. The method of claim 36, wherein the at least one treatment option that is performed is selected from the group of treatment options consisting of an angioplasty, a stent, a pharmaceutical, and combinations thereof.

38. The method of claim 21, wherein the graph comprises a plot of numerical values of the pressure ratios, and wherein the one or more treatment options are simulated by modifying the numerical values of the plot.

39. The method of claim 1, wherein modifying the graph to simulate the one or more treatment options comprises modifying the graph to simulate:
   the one or more treatment options performed at a first region of interest of the vessel; and
   the one or more treatment options performed at a second region of interest of the vessel.

40. The method of claim 1, wherein the graphical representation comprises a plot of pressure ratios along a length of the vessel based on the obtained pressure measurements, and wherein changing the shape of the graphical representation comprises changing the shape of the plot at a location of the plot corresponding to a region of interest in the vessel to simulate the one or more treatment options performed at the region of interest.

41. The method of claim 40, wherein changing the shape of the graphical representation comprises changing a slope at the location of the plot corresponding to the region of interest.

* * * * *